US008728065B2

(12) United States Patent
Fish et al.

(10) Patent No.: US 8,728,065 B2
(45) Date of Patent: May 20, 2014

(54) APPARATUS AND METHODS FOR CONTACTLESS ELECTROPHYSIOLOGY STUDIES

(75) Inventors: Jeffrey Michael Fish, Maple Grove, MN (US); Sacha Christopher Hall, Minneapolis, MN (US); Theodore Arthur Johnson, St. Paul, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 531 days.

(21) Appl. No.: 12/496,855

(22) Filed: Jul. 2, 2009

(65) Prior Publication Data

US 2011/0004087 A1    Jan. 6, 2011

(51) Int. Cl.
  *A61B 18/18* (2006.01)
  *A61B 5/0452* (2006.01)
  *A61B 5/0402* (2006.01)

(52) U.S. Cl.
  USPC ............. 606/32; 600/372; 600/374; 600/381; 606/34

(58) Field of Classification Search
  USPC ................. 606/32–49; 600/372, 374, 381
  See application file for complete search history.

(56) References Cited

U.S. PATENT DOCUMENTS

| 4,860,769 A * | 8/1989 | Fogarty et al. ................. 607/119 |
|---|---|---|
| 5,025,786 A | 6/1991 | Siegel |
| 5,643,255 A * | 7/1997 | Organ ............................. 606/41 |
| 5,680,860 A | 10/1997 | Imran |
| 6,200,315 B1 * | 3/2001 | Gaiser et al. ..................... 606/41 |
| 6,213,995 B1 * | 4/2001 | Steen et al. ..................... 604/527 |
| 6,314,962 B1 * | 11/2001 | Vaska et al. .................... 128/898 |
| 6,839,588 B1 | 1/2005 | Rudy |
| 7,081,115 B2 * | 7/2006 | Taimisto ......................... 606/41 |
| 7,628,801 B2 * | 12/2009 | Westlund et al. .............. 607/112 |
| 2005/0065420 A1 * | 3/2005 | Collins et al. .................. 600/374 |
| 2011/0160593 A1 * | 6/2011 | Deno et al. ..................... 600/463 |

FOREIGN PATENT DOCUMENTS

| EP | 1125549 | 8/2001 |
|---|---|---|
| WO | WO-94/21168 | 9/1994 |

* cited by examiner

*Primary Examiner* — Linda C Dvorak
*Assistant Examiner* — Brian M Antiskay
(74) *Attorney, Agent, or Firm* — Wiley Rein LLP

(57) ABSTRACT

An electrophysiology catheter includes an elongate catheter body having an elastically-deformable distal region predisposed to assume a spiral shape and a first plurality of electrodes disposed thereon. Each of the first plurality of electrodes includes an electrically active region limited to the inner surface of the spiral shape for use in non-contact electrophysiology studies. A second plurality of electrodes may also be disposed on the distal region interspersed (e.g., alternating) with the first plurality of electrodes, with each of the second plurality of electrodes having an electrically active region extending into the outer surface of the spiral shape for use in contact electrophysiology studies. The distal region may be deformed into a straight configuration for insertion into and navigation through the patient's vasculature, for example via use of a tubular introducer. As the distal region deploys beyond the distal end of the introducer, it resumes the spiral shape.

19 Claims, 4 Drawing Sheets

APPARATUS AND METHODS FOR CONTACTLESS ELECTROPHYSIOLOGY STUDIES

CROSS-REFERENCE TO RELATED APPLICATIONS

This application is related to U.S. application Ser. No. 12/131,750, filed 2 Jun. 2008, which is a division of U.S. application Ser. No. 11/734,191, filed 11 Apr. 2007, now abandoned, which is a division of U.S. application Ser. No. 09/547,945, filed 12 Apr. 2000, now abandoned, which is a division of U.S. application Ser. No. 09/005,105, filed 9 Jan. 1998, now abandoned, which is a continuation in part of U.S. application Ser. No. 08/387,832, filed 26 May 2005, now U.S. Pat. No. 6,240,307, which is a national stage entry of PCT/US93/09015, filed 23 Sep. 1993, which is a continuation in part of U.S. application Ser. No. 07/950,448, filed 23 Sep. 1992, now U.S. Pat. No. 5,297,549, which is a continuation in part of U.S. application Ser. No. 07/949,690, filed 23 Sep. 1992, now U.S. Pat. No. 5,311,866. Each of the foregoing is hereby expressly incorporated by reference as though fully set forth herein.

BACKGROUND OF THE INVENTION a. Field of the Invention

The instant invention relates to catheters that are used in the human body. In particular, the instant invention relates to an electrophysiology catheter for use in electrophysiology studies, including, without limitation, electrophysiology studies where sensing electrodes are in contact with the tissue being measured and electrophysiology studies where sensing electrodes are not in contact with the tissue being measured. The present invention also relates to methods of manufacturing and using such a catheter.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example a site within the patient's heart.

A typical electrophysiology catheter includes an elongate shaft and one or more electrodes on the distal end of the shaft. The electrodes may be used for ablation, diagnosis, or the like. Oftentimes, these electrodes are ring electrodes that extend about the entire circumference of the catheter shaft. Thus, when the catheter is introduced into the patient's body, there is the potential for the electrodes to come into contact with tissue surfaces.

BRIEF SUMMARY OF THE INVENTION

It is an object of the present invention to provide an electrophysiology catheter including at least some electrodes that do not come into direct contact with cardiac tissue surfaces during an electrophysiology study.

It is another object of the present invention to provide a kit usable in electrophysiology studies where at least some of the sensing electrodes do not come into contact with tissue surfaces during the electrophysiology studies.

Disclosed herein is an electrophysiology catheter including: an elongate catheter body having an elastically-deformable distal region predisposed to assume a spiral shape having an inner surface and an outer surface when in a relaxed condition; and a first plurality of electrodes disposed on the distal region, each of the first plurality of electrodes having an electrically active region limited to the inner surface of the spiral shape. The electrophysiology catheter optionally also includes a second plurality of electrodes disposed on the distal region, each of the second plurality of electrodes having an electrically active region extending into the outer surface of the spiral shape. The first plurality of electrodes and the second plurality of electrodes may alternate (e.g., every other electrode is an electrode from the first plurality of electrodes and vice versa).

A shape memory material may extend through the distal region of the catheter body to predispose the distal region into the spiral shape. Suitable shape memory materials include shape memory metal wires and shape memory polymers. Where a shape memory metal wire is used, at least a portion of the shape memory metal wire may be encased in a polymeric tube.

In alternative embodiments, a spring element may extend through the distal region of the catheter body to predispose the distal region into the spiral shape. In still other alternative embodiments, the distal region of the catheter body may include a polymeric material that is thermoset into the spiral shape.

At least some of the first and/or second pluralities of electrodes may be ring electrodes. With respect to the first plurality of electrodes, portions of the ring electrodes on the outer surface of the spiral shape may be covered by an electrically insulating material so as to limit the electrically active region thereof to the inner surface of the spiral shape. Alternatively, at least some of the first plurality of electrodes may extend about a fraction of the inner surface of the spiral shape (e.g., the electrode itself is limited to the inner surface of the spiral shape).

The spiral shape of the distal region of the catheter body has a central axis, while the elongate catheter has a longitudinal axis. It is desirable for the central axis of the spiral shape to extend continuously from the longitudinal axis of the elongate catheter. That is, it is desirable for the distal region of the catheter body to be substantially centered on the remainder of the catheter body.

In another aspect, a kit for conducting electrophysiology studies includes a guidewire and/or a tubular introducer having an elongate introducer body having a distal end, a proximal end, and a lumen extending from the proximal end to the distal end; and an electrophysiology catheter. The electrophysiology catheter, in turn, includes an elongate catheter body that is deployable through the lumen of the introducer and/or introduceable over the guidewire. The distal region of the catheter body is elastically deformable and predisposed to assume a spiral shape having an inner surface and an outer surface when in a relaxed state unconstrained by either the introducer or the guidewire. The distal region of the catheter body also includes a plurality of electrically active regions, wherein each of the plurality of electrically active regions is limited to the inner surface of the spiral shape. The tubular introducer optionally includes a steering mechanism operable to deflect the distal end of the elongate introducer body in at least one degree of freedom.

Also disclosed herein is a method of conducting an electrophysiological study that includes the following steps: providing an electrophysiology catheter having an elastically deformable distal region predisposed to assume a spiral shape having a central axis when in a relaxed state and including a plurality of electrically active regions facing the central axis of the spiral shape; introducing the electrophysiology catheter into a patient; and gathering electrophysiological data using the plurality of electrically active regions without bringing the electrically active regions into contact with tissue.

Typically, the step of introducing the electrophysiology catheter into a patient comprises introducing the electrophysiology catheter into the patient via the patient's vasculature. It may also include: inserting the electrophysiology catheter into a tubular introducer, thereby causing the distal region of the electrophysiology catheter to assume a collapsed shape conforming to the introducer; introducing the introducer with the electrophysiology catheter inserted therein into the patient; navigating the introducer with the electrophysiology catheter inserted therein to a first location of interest; and deploying the distal region of the electrophysiology catheter from the tubular introducer at the first location of interest, thereby causing the distal region of the electrophysiology catheter to resume the spiral shape.

The method may optionally include the following steps: retracting the distal region of the electrophysiology catheter into the tubular introducer, thereby causing the distal region of the electrophysiology catheter to resume the collapsed shape; navigating the introducer with the electrophysiology catheter inserted therein to an additional location of interest; and deploying the distal region of the electrophysiology catheter from the tubular introducer at the additional location of interest, thereby causing the distal region of the electrophysiology catheter to resume the spiral shape.

In yet another aspect, a method of manufacturing an electrophysiology catheter includes the steps of: forming an elongate catheter body having an elastically deformable distal region; predisposing the distal region of the elongate catheter body to assume a spiral shape when in a relaxed state; and mounting a plurality of electrodes to the distal region of the elongate catheter body, each of the plurality of electrodes having an electrically active region limited to an inner surface of the spiral shape. The step of predisposing the distal region of the elongate catheter body to assume a spiral shape when in a relaxed state may include placing a shape memory metal wire having a memory shape corresponding to the spiral shape into the distal region of the elongate catheter body. Alternatively, the step of predisposing the distal region of the elongate catheter body to assume a spiral shape when in a relaxed state may include placing a spring temper wire biased into the spiral shape into the distal region of the elongate catheter body.

Devices and methods according to the present invention advantageously permit the conduct of electrophysiology studies, such as the generation of heart chamber maps, without bringing sensing electrodes into contact with a tissue surface.

Another advantage of devices and methods according to the present invention is enhanced compatibility with localization systems, such as the EnSite NavX™ navigation and visualization system of St. Jude Medical, Atrial Fibrillation Division, Inc.

The foregoing and other aspects, features, details, utilities, and advantages of the present invention will be apparent from reading the following description and claims, and from reviewing the accompanying drawings.

DETAILED DESCRIPTION OF THE INVENTION

The present invention will be described with reference to an electrophysiology catheter utilized in cardiac electrophysiology studies. It should be understood, however, that the present teachings may be applied to good advantage in other contexts as well.

Figure 1:
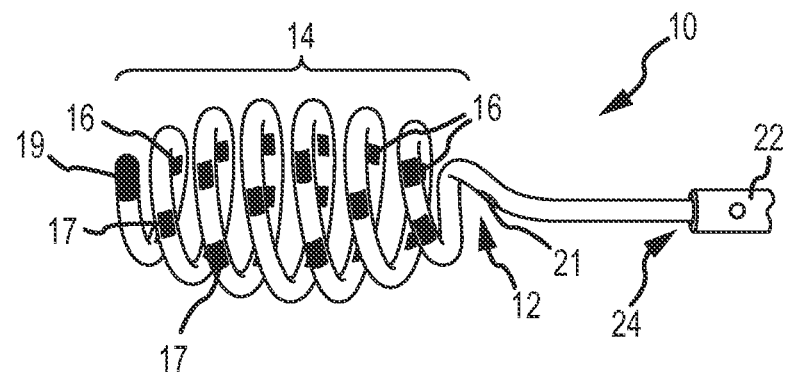
FIG. 1 is a side view of a representative electrophysiology catheter having a spiral-shaped distal region and interior-facing electrically active regions. Also visible in FIG. 1 is an exemplary introducer catheter.
Figure 2:
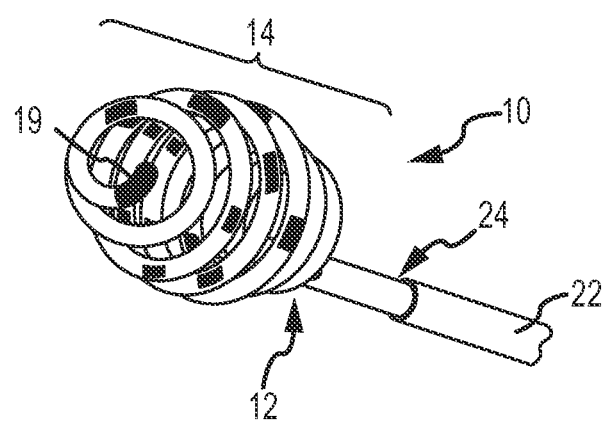
FIG. 2 is an isometric view of the electrophysiology catheter and introducer catheter of FIG. 1.

Referring now to the figures, FIGS. 1 and 2 depict an electrophysiology ("EP") catheter 10 according to a first aspect of the present invention. FIG. 1 is a side view of EP catheter 10, while FIG. 2 is a perspective view of EP catheter 10.

EP catheter 10 generally includes an elongate catheter body 12 having a distal region 14. EP catheter 10 will typically be made of a biocompatible polymeric material, such as polytetrafluoroethylene (PTFE) tubing (e.g., TEFLON® brand tubing). Of course, other polymeric materials, such as fluorinated ethylene-propylene copolymer (FEP), perfluoroalkoxyethylene (PFA), poly(vinylidene fluoride), poly(ethylene-co-tetrafluoroethylene), and other fluoropolymers, may be utilized. Additional suitable materials for catheter body 12 include, without limitation, polyamide-based thermoplastic elastomers (namely poly(ether-block-amide), such as PEBAX®), polyester-based thermoplastic elastomers (e.g., HYTREL®)., thermoplastic polyurethanes (e.g., PELLETHANE®, ESTANE®), ionic thermoplastic elastomers, functionalized thermoplastic olefins, and any combinations thereof. In general, suitable materials for EP catheter 10 may also be selected from various thermoplastics, including, without limitation, polyamides, polyurethanes, polyesters, functionalized polyolefins, polycarbonate, polysulfones, polyimides, polyketones, liquid crystal polymers and any combination thereof. It is contemplated that the durometer of catheter body 12 may vary along its length.

At least distal region 14 of catheter body 12 is elastically deformable. That is, distal region 14 can be deformed into different shapes, but will substantially return to its relaxed shape when the deforming force is removed. Preferably, and as seen in FIGS. 1 and 2, the relaxed shape of distal region 14 is a multi-loop spiral shape. That is, during manufacture (e.g., using a shaped mandrel or other suitable tooling), distal region 14 is predisposed to assume a multi-loop spiral shape when no forces are applied thereto. In some embodiments of the invention, the various loops of the multi-loop spiral shape may have varying diameters. It is also desirable for the remainder of catheter body 12 to be flexible so that it can be navigated through a patient's vasculature to a location of interest as described below.

As used herein, the terms "spiral shape" and "multi-loop spiral shape" refer to a shape that spirals about and extends along a central axis. In other words, the terms "spiral shape" and "multi-loop spiral shape" both refer to three-dimensional shapes.

Several variations on the multi-loop spiral shape of distal region 14 are suitable for use in connection with the present invention. For example, the spiral shape may generally resemble a football, a hard-boiled egg, a barrel, a sphere, an ellipsoid, an oblate spheroid, a regular or irregular organic mushroom shape, conical shapes (e.g., shapes that monotonically taper either towards or away from the distal end of distal region 14) or any other desirable shapes. One of ordinary skill in the art will appreciate from this disclosure how to select a suitable spiral shape for a particular application of EP catheter 10.

Figure 3:
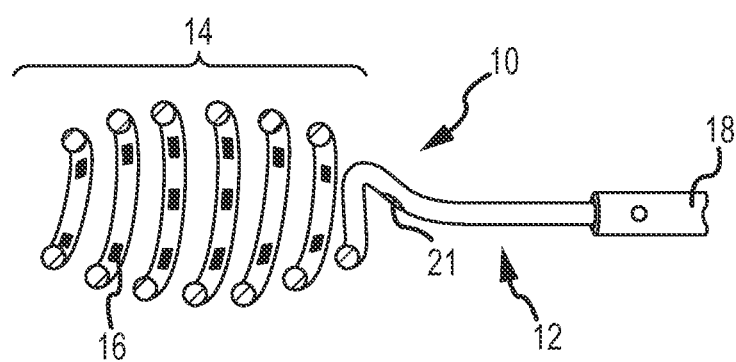
FIG. 3 is a partial cutaway side view of the electrophysiology catheter depicted in FIG. 1.

The shape of distal region 14 defines both an inner surface (e.g., that portion of the circumference of catheter body 12 that generally faces the central axis of distal region 14) and an outer surface (e.g., that portion of the circumference of catheter body 12 that generally faces away from the central axis of distal region 14). A plurality of electrodes 16 are disposed on distal region 14, and, in some aspects of the invention, each of the plurality of electrodes 16 has an electrically active region that is limited to the inner surface of the spiral shape as shown in the cutaway of EP catheter 10 illustrated in FIG. 3. Thus, when EP catheter 10 is introduced into a patient's heart chamber, the electrically active regions of electrodes 16 will not come into contact with cardiac tissue even if the outer surface of distal region 14 does contact a cardiac surface. It is also desirable for the central axis of the spiral shape to extend continuously from the longitudinal axis of the elongate catheter (e.g., for the straight, proximal portion of catheter body 12 to be generally centered on the spiral shape of distal region 14).

The electrically active regions of electrodes 16 may be defined by utilizing ring electrodes that are partially masked or insulated, for example by covering the portions of electrodes 16 on the outer surface of the spiral shape with a dielectric material, polyester heat shrink tubing, or another suitable electrically insulating material. Alternatively, the electrodes may be sized such that they extend only about the inner surface of the spiral shape (e.g., partial ring electrodes), such that the entire surface of the electrode is the electrically active region. Of course, a combination of masked/insulated ring, partial ring, or other types of electrodes (e.g., button- or spot-type electrodes) may be utilized without departing from the present invention. Combinations of electrode types can also be used either simultaneously or serially, as desired. In some embodiments of the invention, distal region 14 may include up to sixty-four electrodes 16, though this embodiment is merely illustrative and more or fewer electrodes may be utilized consistent with the present teachings.

In other embodiments of the invention, distal region 14 may also include one or more additional electrodes 17 having electrically active regions that extend beyond the inner surface of the spiral shape. In certain aspects, electrodes 16 may alternate with electrodes 17 (e.g., every other electrode on distal region 14 has an electrically active region generally limited to the inner surface of the spiral shape). A suitable switching mechanism may also be provided to permit manual or automatic toggling between a first operating condition where electrodes 16 are active and a second operating condition where electrodes 17 are active. Such a configuration advantageously allows EP catheter 10 to be used in both contact and non-contact electrophysiology studies and ablated via electrodes 17.

In still other embodiments, EP catheter 10 may be modified for use in therapeutic procedures in addition to electrophysiology studies. For example, EP catheter 10 may be used first to map cardiac activity and then to ablate tissue to treat a detected arrhythmia. Thus, EP catheter 10 may include a tip electrode 19 usable to deliver ablative energy to adjacent cardiac tissue. Tip electrode 19 may be between about 2 mm and about 8 mm long. It is also contemplated that tip electrode 19 may be irrigated. Of course, alternative ablating elements (e.g., high intensity focused ultrasound ("HIFU"), laser, microwave, cryogenic, and the like) may be utilized instead of tip electrode 19. It is also contemplated that electrodes 17 may be used to deliver ablative energy.

As generally known in the art, electrodes 16 and 19 may be used to measure electrophysiology data from the surface of the heart as part of a cardiac mapping procedure or other electrophysiology study. Electrodes 16 may also be utilized in conjunction with a localization system, such as the EnSite NavX™ navigation and visualization system of St. Jude Medical, Atrial Fibrillation Division, Inc., to localize (that is, to determine the position and/or orientation of) EP catheter 10 within a patient's body. Accordingly, each electrode 16 may be coupled to one or more lead wires 17 (FIG. 6); these lead wires may be routed back to the proximal end of elongate catheter body 12 via a lumen 18 (FIGS. 3 and 6) extending therethrough. Alternatively, the lead wires may be embedded in the wall of elongate catheter body 12. For example, U.S. application Ser. No. 11/646,578, filed 28 Dec. 2006 and incorporated by reference as though fully set forth herein, discloses a method of substantially embedding electrode lead wires in a catheter wall structure. Other localization systems may also be used in connection with the present invention, including for example, the CARTO navigation and location system of Biosense Webster, Inc., the AURORA® system of Northern Digital Inc., Sterotaxis' NIOBE® Magnetic Navigation System, or St. Jude Medical's MediGuide Medical Positioning System, all of which utilize magnetic fields rather than electrical fields.

Figure 4:
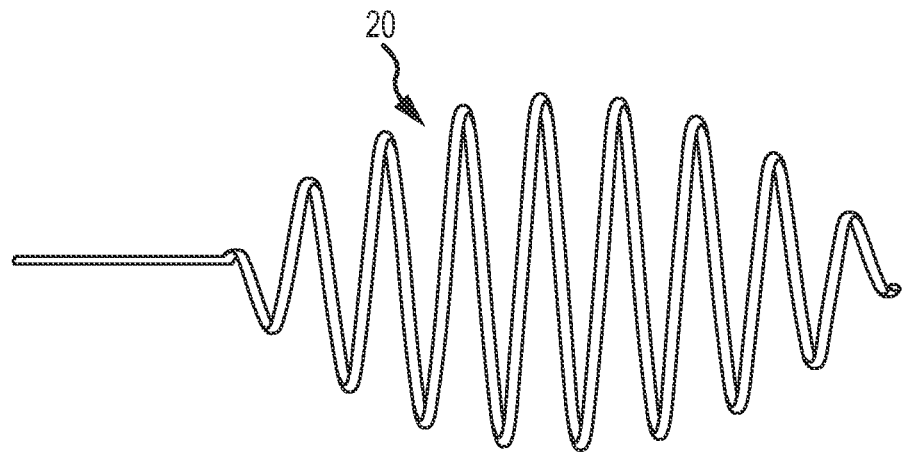
FIG. 4 is a side view of a representative shaping wire that can be used to predispose an electrophysiology catheter according to the present invention to assume a desired spiral shape.
Figure 5:
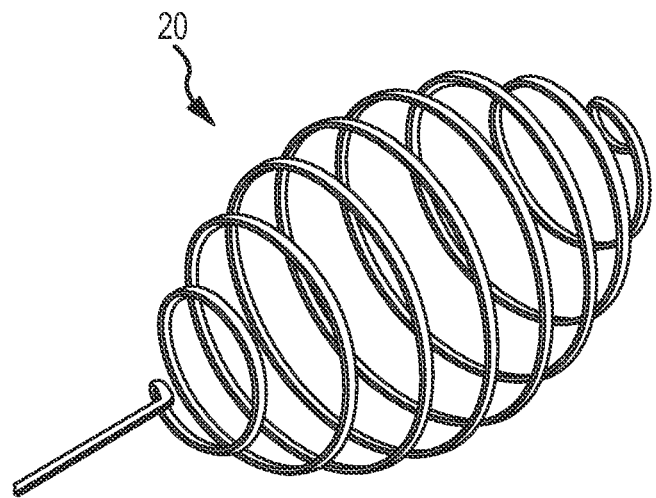
FIG. 5 is an isometric view of the representative shaping wire depicted in FIG. 4.

In some aspects of the invention, a shaping wire 20 (FIGS. 4 and 5) is utilized to predispose distal region 14 into the desired shape. Shaping wire 20 may optionally be a shape memory metal wire, for example a wire comprising an alloy of nickel and titanium (known commercially as NiTi or Nitinol), which helps distal region 14 of EP catheter 10 retain its desired shape. Alternatively, shaping wire 20 could be a strip of stainless steel or another resilient metal in the nature of a spring temper wire or spring element. In still other embodiments, shaping wire 20 could be a plastic material (e.g., a thermoset material or a shape memory plastic or polymer) or a combination of resin-based materials and shaping wires. FIGS. 4 and 5 illustrate one suitable shaping wire 20 in side and perspective views, respectively. Shaping wire 20 can be coupled to one or more anchor members (not shown), to electrodes 16, or to other structures within EP catheter 10.

It should also be understood that distal region 14 of EP catheter 10 may include multiple shaping wires. One of ordinary skill in the art will appreciate how to utilize one or more shaping wires to predispose distal region 14 into the desired spiral shape.

The term "shaping wire" is used herein to describe a strip of material (e.g., a circular or flat wire) that, after deformation, returns to its former shape. The term "shape memory wire" is used herein to refer to a wire that has been deformed to a certain shape and briefly heated to fix that shape. The wire possesses a memory causing it to return to its fixed shape after being deformed. If the wire returns to its former shape without first being heated to a certain transition temperature, it may be referred to as a "superelastic shape memory wire." Both superelastic and non-superelastic materials, however, are contemplated for use as shaping wire 20.

Figure 6:
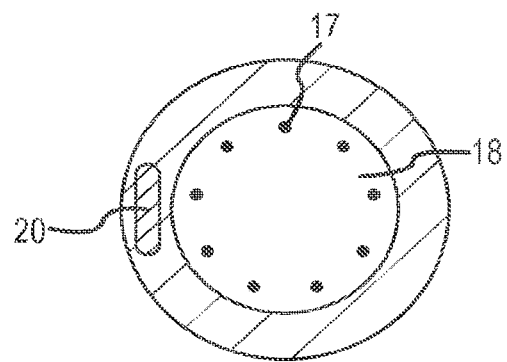
FIG. 6 is an axial cross section of the distal region of an electrophysiology catheter according to some embodiments of the present invention, including a shaping wire embedded in the catheter wall.
Figure 7:
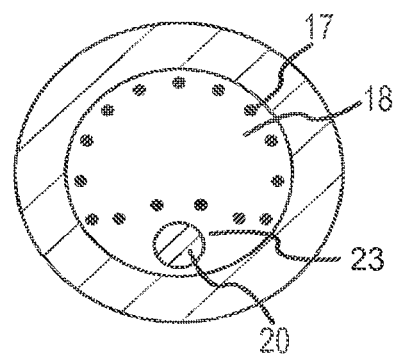
FIG. 7 is an axial cross section of the distal region of an electrophysiology catheter according to other embodiments of the present invention, including a shaping wire encased in a polymeric tube.

In some embodiments of the invention, such as the embodiment of the invention illustrated in FIG. 6, shaping wire 20 will be embedded in the wall of catheter body 12 throughout distal region 14. Alternatively, shaping wire 20 may be encased in a polymeric tube 23 that is suitably bonded to catheter body 12 (e.g., to the inner wall of lumen 18), for example as illustrated in FIG. 7. Of course, it is also within the scope of the present invention for a first portion of shaping wire 20 to be encased in a polymeric tube and for a second portion of shaping wire 20 to be embedded in the wall of catheter body 12.

In another aspect of the present invention, no shaping wire is used to predispose distal region 14 into the spiral shape. Instead, distal region 14 is thermoset into the spiral shape.

Catheter body 12 may optionally include a working port 21 near distal region 14. Working port 21 facilitates the introduction of additional devices, such as transducers and imaging devices, through catheter body 12. In some embodiments of the invention, working port 21 passes a push/pull element (not shown), the end of which is coupled to the distal end of distal region 14 in order to "fine tune" the shape of distal region 14 for a particular application. One of ordinary skill in the art will recognize that, by pushing the push/pull element, the spiral shape of distal region 14 will become longer and thinner (e.g., the radius of the spiral will tighten), as if the points of a football were pulled apart from each other. Conversely, by pulling the push/pull element, the spiral shape of distal region 14 will become shorter and wider (e.g., the radius of the spiral will expand), as if the points of a football were pushed towards each other.

EP catheter 10 may be included as part of a kit for conducting cardiac electrophysiology studies. In addition to EP catheter 10, such a kit generally includes an elongate tubular introducer 22, visible in FIGS. 1 and 2, having a distal end 24, a proximal end (not shown), and a lumen extending from the distal end to the proximal end. Any suitable introducer may be employed as part of a kit for conducting cardiac electrophysiology studies provided it has an outer diameter sufficiently small to navigate the patient's vasculature (e.g., less than about 12 French, and more preferably less than about 10 French) and an inner diameter sufficiently large to accommodate EP catheter 10. In some embodiments, introducer 22 includes a steering mechanism (not shown) operable to deflect distal end 24 of introducer 22 in at least one degree of freedom in order to facilitate navigating introducer 22 through the patient's vasculature. For example, Patent Cooperation Treaty application no. PCT/US08/54149, filed 15 Feb. 2008 and published on 21 Aug. 2008 as WO/2008/101206, discloses steerable introducer catheters that may be included in a kit according to certain embodiments of the present invention. PCT/US08/54149 is hereby incorporated by reference as though fully set forth herein.

Catheter body 12 of EP catheter 10 can be inserted into the lumen of introducer 22. Because distal region 14 of catheter body 12 is elastically deformable, distal region 14 of catheter body 12 will substantially conform to the shape of introducer 22 when inserted therein. This facilitates navigating introducer 22 and EP catheter 10 through the patient's vasculature to a desired location. When distal region 14 of catheter body 12 is extended distally from distal end 24 of introducer 22, however, it will resume the spiral shape as shown in FIGS. 1 and 2. To aid the practitioner in determining how far beyond distal end 24 of introducer 22 catheter body is extended, the proximal end (e.g., the handle) of EP catheter 10 and/or introducer 22 may include suitable indices. Alternatively, or in addition, fluoroscopic imaging or another suitable imaging modality may be employed to visualize the deployment of EP catheter 10 from introducer 22.

In use, EP catheter 10 is introduced into a patient, for example into one of a patient's heart chambers. It is desirable for EP catheter 10 to be introduced into the patient in a substantially straight configuration, as this minimizes the size of the necessary incision and reduces the trauma to the patient. Typically, therefore, EP catheter 10 is inserted into introducer 22, thereby causing distal region 14 of catheter body 12 to assume a collapsed shape substantially conforming to that of introducer 22. The two devices can then be navigated through the patient's vasculature until distal end 24 of introducer 22 is in the chamber of interest. With distal end 24 of introducer 22 in position, distal region 14 of EP catheter 10 can be deployed from distal end 24 of introducer 22, either by advancing EP catheter 10 distally or by retracting introducer 22 proximally. As distal region 14 of EP catheter 10 emerges from introducer 22, it will return to the spiral shape into which it is predisposed.

With distal region 14 deployed in the chamber of interest, electrophysiological data can be gathered using electrodes 16, 17, and/or 19. As described above, this data can be gathered without bringing the electrically active regions of electrodes 16 into contact with cardiac tissue. In some embodiments, a suitable controller may be employed to allow a practitioner to disable electrodes 16, 17, and/or 19 that are not advantageously positioned. Alternatively, a push/pull element coupled to the distal end of catheter body 12 and passed through working port 21 may be used to elongate or compress distal region 14 in order to "fine tune" the position of electrodes 16, 17, and/or 19.

Once the first heart chamber has been mapped, distal region 14 may be re-deployed into introducer 22, for example by retracting EP catheter 10 proximally or by advancing introducer 22 distally. This will return distal region 14 to the collapsed shape substantially conforming to the shape of introducer 22, which permits the two devices to once again be navigated through the patient's vasculature to a second of the patient's heart chambers. With distal end 24 of introducer 22 in place in the second heart chamber, distal region 14 may once again be deployed out of introducer 22, where it resumes the spiral shape, in order to gather additional electrophysiological data. This process may be repeated many times, enabling EP catheter 10 to gather electrophysiological data at any number of locations of interest. Indeed, it is contemplated that EP catheter 10 may also be introduced into certain locations of interest through a transeptal puncture. Of course, EP catheter 10 and/or introducer 22 may be independently deflected to enhance intravascular and in-chamber navigation and placement of distal region 14.

Although several embodiments of this invention have been described above with a certain degree of particularity, those skilled in the art could make numerous alterations to the disclosed embodiments without departing from the spirit or scope of this invention. For example, though EP catheter 10 and introducer 22 are described above as being simultaneously introduced into the patient's vasculature, alternative methods of introducing EP catheter 10 into the patient are contemplated. For example, introducer 22 may be navigated to the desired location first (e.g., introduced over a guidewire or using a stylet), and then EP catheter 10 may be inserted into introducer 22. As another example, EP catheter 10 may be introduced into the patient without the use of introducer 22, such as by using a stylet or other straightening device to place distal portion 14 into the collapsed configuration.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electrophysiology catheter, comprising: an elongate catheter body comprising an elastically-deformable distal region including a portion predisposed to assume a spiral shape comprising an inner surface on an inside of the spiral shape configured not to contact tissue and an outer surface on an outside of the spiral shape capable of contacting tissue when in a relaxed condition, the distal region terminating in a distal tip; and a plurality of electrodes disposed on the distal region, each of the plurality of electrodes comprising an electrically active region, wherein there are no electrically active regions on the outer surface of the spiral shaped portion of the distal region.

2. The electrophysiology catheter according to claim 1, further comprising a shape memory material extending through the distal region of the catheter body to predispose the spiral shaped portion of the distal region into the spiral shape.

3. The electrophysiology catheter according to claim 2, wherein the shape memory material comprises a shape memory metal wire.

4. The electrophysiology catheter according to claim 3, further comprising a polymeric tube, and wherein at least a portion of the shape memory metal wire is encased in the polymeric tube.

5. The electrophysiology catheter according to claim 2, wherein the shape memory material comprises a shape memory polymer.

6. The electrophysiology catheter according to claim 1, further comprising a spring element extending through the distal region of the catheter body to predispose the spiral shaped portion of the distal region into the spiral shape.

7. The electrophysiology catheter according to claim 1, wherein the distal region of the catheter body comprises a polymeric material thermoset into the spiral shape.

8. The electrophysiology catheter according to claim 1, wherein at least some of the plurality of electrodes comprise ring electrodes, wherein portions of the ring electrodes on the outer surface of the spiral shape are covered by an electrically insulating material.

9. The electrophysiology catheter according to claim 1, wherein at least some of the plurality of electrodes extend about a fraction of the inner surface of the spiral shape.

10. The electrophysiology catheter according to claim 1, wherein the spiral shape has a central axis, the elongate catheter has a longitudinal axis, and the central axis of the spiral shape extends continuously from the longitudinal axis of the elongate catheter.

11. A kit for conducting electrophysiology studies, comprising: at least one of a guidewire and a tubular introducer comprising an elongate introducer body comprising a distal end, a proximal end, and a lumen extending from the proximal end to the distal end; and an electrophysiology catheter comprising an elongate catheter body adapted to be one of deployed through the lumen of the introducer or introduced over the guidewire and comprising an elastically-deformable distal region predisposed to assume a spiral shape having an inner surface on an inside of the spiral shape configured not to contact tissue and an outer surface on an outside of the spiral shape capable of contacting tissue when the distal region of the elongate catheter body is in a relaxed state unconstrained by the introducer body or guidewire; a plurality of electrically active regions on the distal region of the elongate catheter body, wherein each of the plurality of electrically active regions is limited to the inner, non-tissue-contacting surface of the spiral shape; and wherein there are no electrically active regions on the outer surface of the spiral shape.

12. The kit according to claim 11, wherein at least some of the plurality of electrically active regions comprise ring electrodes having an electrically insulating material covering portions of the ring electrodes on the outer surface of the spiral shape.

13. The kit according to claim 11, wherein the tubular introducer includes a steering mechanism operable to deflect the distal end of the elongate introducer body in at least one degree of freedom.

14. The electrophysiology catheter according to claim 1, wherein the distal tip includes a tip electrode.

15. The electrophysiology catheter according to claim 1, wherein the spiral shaped portion of the distal region includes at least two turns about and extending along a central axis.

16. An electrophysiology catheter, comprising: an elongate catheter body comprising an elastically-deformable distal region predisposed to assume a three-dimensional shape surrounding and extending along a central axis when in a relaxed condition, the distal region having an inner surface on an inside of the three-dimensional shape that faces the central axis and is configured not to contact tissue and an outer surface on an outside of the three-dimensional shape capable of contacting tissue; and a plurality of electrodes disposed on the distal region, each of the plurality of electrodes comprising an electrically active region, wherein the outer surface of the distal region is devoid of electrically active regions.

17. The electrophysiology catheter according to claim 16, wherein the three-dimensional shape comprises a spiral shape.

18. The electrophysiology catheter according to claim 16, wherein the elongate catheter body terminates in a distal tip comprising a tip electrode.

19. The electrophysiology catheter according to claim 16, wherein the entirety of the outer surface of the three-dimensional shape is devoid of electrically active regions.

* * * * *